(12) United States Patent
Driemel et al.

(10) Patent No.: US 12,097,019 B2
(45) Date of Patent: Sep. 24, 2024

(54) MAGNETIC RESONANCE LOCAL COIL HAVING ROTATABLE CONNECTION CABLE

(71) Applicant: Siemens Healthcare GmbH, Erlangen (DE)

(72) Inventors: Daniel Driemel, Dederan (DE); Stephan Zink, Nuremberg (DE); Martin Hemmerlein, Bamberg (DE)

(73) Assignee: Siemens Healthineers AG, Forchheim (DE)

(*) Notice: Subject to any disclaimer, the term of this patent is extended or adjusted under 35 U.S.C. 154(b) by 48 days.

(21) Appl. No.: 17/947,457

(22) Filed: Sep. 19, 2022

(65) Prior Publication Data

US 2023/0104451 A1    Apr. 6, 2023

(30) Foreign Application Priority Data

Sep. 28, 2021  (EP) ..................................... 21199517

(51) Int. Cl.
*G01V 3/00* (2006.01)
*A61B 5/055* (2006.01)
*G01R 33/32* (2006.01)

(52) U.S. Cl.
CPC .............. *A61B 5/055* (2013.01); *G01R 33/32* (2013.01)

(58) Field of Classification Search
CPC . G01N 24/10; G01R 29/0807; G01R 33/4608
USPC ....................................................... 324/309
See application file for complete search history.

(56) References Cited

U.S. PATENT DOCUMENTS

| | | |
|---|---|---|
| 2016/0047868 A1 | 2/2016 | Driemel |
| 2017/0074954 A1 | 3/2017 | Rehner |
| 2017/0082705 A1 | 3/2017 | Hou et al. |
| 2017/0227500 A1* | 8/2017 | Borigo ............... G01N 29/2462 |
| 2018/0301818 A1* | 10/2018 | Welle ..................... G01S 13/88 |

FOREIGN PATENT DOCUMENTS

| | | | | |
|---|---|---|---|---|
| CN | 108601925 A | * | 9/2018 | ....... A61B 17/00234 |
| CN | 109038085 A | * | 12/2018 | ........... H01R 13/627 |
| DE | 102014216077 A1 | | 2/2016 | |
| DE | 102015217325 A1 | | 3/2017 | |
| DE | 102017100056 A1 | * | 7/2018 | |
| JP | H09504 A | | 1/1997 | |
| JP | 2008154933 A | | 7/2008 | |
| JP | 2010093359 A | * | 4/2010 | |
| JP | 2012019419 A | * | 1/2012 | |

* cited by examiner

*Primary Examiner* — Walter L Lindsay, Jr.
*Assistant Examiner* — Frederick Wenderoth
(74) *Attorney, Agent, or Firm* — Lempia Summerfield Katz LLC (57) ABSTRACT

A magnetic resonance (MR) local coil and a magnetic resonance apparatus are disclosed. The MR local coil includes an antenna unit having at least one antenna for receiving and/or transmitting high frequency (HF) signals; a connection cable for connecting the MR local coil to a magnetic resonance apparatus; and a two-dimensional, (e.g., ribbon-shaped), transmission element for transmitting energy, (e.g., electrical energy), and/or signals, (e.g., electrical and/or optical signals), between the connection cable and the antenna unit. In this case, the transmission element is at least in part arranged about an axis of rotation in a spiral manner.

19 Claims, 6 Drawing Sheets

FIG 1

10 Magnetic resonance apparatus
11 Magnet unit
12 Main magnet
13 Main magnetic field
14 Patient receiving region
15 Patient
16 Patient positioning apparatus
17 Patient table
18 Gradient coil unit
19 Gradient control unit
20 HF antenna unit
21 HF antenna control unit
22 System control unit
23 User interface
24 Display unit
25 Input unit
26 Plug socket
100 MR local coil
107 2D transmission element
116 Connection cable
120 Antenna unit

FIG 2

101 First housing part
102 Further housing part
104 Tongue and groove connection
113 Plug or socket
114 Circuit board
115 Socket or plug
116 Connection cable
117 Recess

FIG 3

101 First housing part
102, 103 Further housing part
107 Transmission element
114 Circuit board
116 Connection cable

FIG 4

105 Rigid-flexible circuit board
106 Rigid part
107 Transmission element
108 Rigid part
113 Plug or socket

FIG 5

107 Transmission element
112 Limiting element

114 Circuit board
115 Socket or plug
117 Recesses
118 Guiding element
119 Gap

FIG 8

MAGNETIC RESONANCE LOCAL COIL HAVING ROTATABLE CONNECTION CABLE

The present patent document claims the benefit of European Patent Application No. 21199517.0, filed Sep. 28, 2021, which is hereby incorporated by reference in its entirety.

TECHNICAL FIELD

The disclosure relates to a magnetic resonance (MR) local coil and a magnetic resonance apparatus.

BACKGROUND

In medical technology, imaging by magnetic resonance (MR), also known as magnetic resonance tomography (MRT) or magnetic resonance imaging (MRI), is characterized by high soft tissue contrasts. In this case, with the aid of a magnetic resonance apparatus, excitation pulses are irradiated into an object that is to be examined, (e.g., a patient). As a consequence, magnetic resonance signals are triggered in the patient. The magnetic resonance signals are received as measurement data by the magnetic resonance apparatus and are used for the reconstruction of magnetic resonance imaging.

The magnetic resonance signals may be received using so-called local coils, (e.g., surface coils). Such MR local coils may include one or multiple MR antennas and are attached in the immediate vicinity of the patient during a magnetic resonance examination.

A conventional MR local coil may have an electrical connection to the magnetic resonance apparatus for the voltage supply and signal transmission. This may be realized by a connection cable. The connection cable emerges from the local coil and is contacted by a plug connection to the magnetic resonance apparatus. In order to examine the patient, local coils are also placed on the patient. The local coils may cover a part of the body of the patient and are not limited to a fixed position relative to the patient in dependence upon the region that is to be examined. In the case of MR local coils that may be flexibly positioned relative to the patient, there is a different guiding arrangement of the connection cable depending on how the MR local coil is arranged on the patient.

SUMMARY AND DESCRIPTION

An object of the present disclosure is to simplify the handling of an MR local coil, in particular, the cable guiding arrangement.

The scope of the present disclosure is defined solely by the appended claims and is not affected to any degree by the statements within this summary. The present embodiments may obviate one or more of the drawbacks or limitations in the related art.

Accordingly, an MR local coil is provided that includes an antenna unit having at least one antenna for receiving and/or transmitting high frequency (HF) signals. The MR coil further includes a connection cable for connecting the MR local coil to a magnetic resonance apparatus. The MR coil further includes a two-dimensional, (e.g., ribbon-shaped), transmission element for transmitting energy, (e.g., electrical energy), and/or signals, (e.g., electrical and/or optical signals), between the connection cable and the antenna unit. In this case, the transmission element is at least in part arranged, in particular coiled, about a rotational axis in a spiral manner. Advantageously, the connection cable is configured to be rotated on a connecting site of the connection cable to the antenna element about the axis of rotation relative to the antenna element.

The transmission element may include a coil having at least one-half winding, at least one winding, or at least two windings about the axis of rotation. In particular, the transmission element describes a snail curve within a plane or layer. In particular, the transmission element does not describe a screw, spiral coil, and/or helix.

The transmission element is configured to be two-dimensional. In particular, the transmission element has a small thickness in the direction with respect to the axis of rotation. In particular, the transmission element has a shape of a ribbon. This ribbon may have a thickness that is at least three times or five times smaller than the width of the ribbon. As a consequence, the transmission element may be brought into its spiral shape, in particular, without or with only a small application of (mechanical) force.

The spiral-shaped arrangement of the transmission element may include a curve or a spiral line that extends about the axis of rotation and extends away or approaches in particular along the transmission element from the axis of rotation (e.g., depending on the viewing perspective). Depending on the rotation state, the outer line of this curve may have a smaller or a larger distance with respect to the axis of rotation.

The transmitted HF signals are by way of example excitation signals, (e.g., excitation pulses), for exciting magnetic resonance signals. The received HF signals are by way of example magnetic resonance signals that occur, in particular, in a body of a patient by magnetic resonance.

The magnetic resonance apparatus may include a plug connecting part, in particular a plug socket, and the plug connecting part may form a plug connection with a complementary plug connecting part of the connection cable. It is possible via this plug connection to advantageously transmit the signals and/or energy.

The connection cable and/or the transmission element may have electrical and/or optical conductors in order to transmit the energy and/or the signals.

The connection cable may be arranged on the (remaining) MR local coil in a detachable manner, in other words, the connection cable may be removed without damaging the MR local coils.

The axis of rotation may be arranged perpendicular to a surface, (e.g., a two-dimensional surface), of the antenna unit. This surface may have a large expansion with respect to possible other surfaces of the MR local coil. Advantageously, the connection cable may be rotated on the connecting site to the antenna unit.

The antenna unit of freely placeable MR local coils, (e.g., a so-called body array), may be used on the patient in different relative positions, for example, rotated about 0° or 90°. Consequently, such an MR local coil in contrast to the example of an MR head coil, (which may not be freely placed), may change its position and distance with respect to its plug socket on the magnetic resonance apparatus. (The plug socket may be arranged on the patient table of the magnetic resonance apparatus.) It is possible, owing to the now possible rotation of the connection cable, to keep the length of the connection cable particularly short, whereby it is advantageously also possible to reduce the weight of the MR local coil. The safety of the patient may also be increased if it is possible to avoid a looping on the patient by avoiding an excessively long cable.

Moreover, the ability to rotate renders possible an increased flexibility in the handling of the MR local coil, in particular, in its placement on the body of the patient. Advantageously, the guiding arrangement of the connection cable may be arranged, in particular, on the body of the patient in a more patient friendly manner.

A further embodiment of the MR local coil provides that the transmission element includes a flexible circuit board. The flexible circuit board may be single-layered or multi-layered. The circuit board may include an impedance-controlled layer, e.g., a 50 ohm layer. The flexible circuit board may have a thickness of 0.1 to 2 mm, 0.2 to 0.8 mm, or 0.4 mm. The normal of the (e.g., two-dimensional) surface of the circuit board may be perpendicular with respect to the axis of rotation.

Owing to the small thickness of the circuit board and/or its flexible material characteristics, it is advantageously possible for the flexible circuit board to easily wind about the axis of rotation. The electrical conductor tracks, (e.g., made of copper), may be applied to the flexible circuit board and signals and/or energy may be transmitted via the conductor tracks.

A further embodiment of the MR local coil provides that the transmission element includes a ribbon cable. The ribbon cable may be a multi-wired cable in which the leads are guided parallel to one another. Signals and/or energy may be transmitted via the leads. Advantageously, the ribbon cable may be easily wound about the axis of rotation in a spiral manner.

A further embodiment of the MR local coil provides that the antenna unit includes multiple antennas, (e.g., coil elements), wherein the transmission element includes multiple electrical and/or optical conductors, which are arranged adjacent to one another, in order to transmit the signals of the multiple antennas. These conductors may be configured as conductor tracks on a flexible circuit board and/or as leads in a ribbon cable.

Each antenna of the multiple antennas may be allocated to a channel, e.g., a transmitting channel and/or a receiving channel. If the antenna unit includes, for example, 16 antennas, it is possible to speak of a 16-channel MR local coil.

In addition to the conductors that are allocated to a specific channel, the transmission element may also include further conductors by which control information, coil identification data, and/or electrical power may be transmitted.

A further embodiment of the MR local coil provides that the antenna unit is configured as two-dimensional and/or flexible, e.g., in the form of a cover. MR local coils having an antenna unit of this type particularly benefit from the rotatability of the connection cable because these local coils may be placed in particularly different orientations on the patient. Advantageously, owing to the proposed connection of the connection cable to the antenna unit, it is no longer necessary to stow an excessive amount of connection line and the connection line does not deform the flexible antenna unit at the coil connection on account of a position that is not optimal.

A further embodiment of the MR local coil provides that the MR local coil includes a housing having a first housing part and a second housing part, wherein the transmission element is arranged in the housing, wherein the second housing part may be rotated relative to the first housing part about the axis of rotation.

The first and the second housing parts may be rigid. The housing advantageously protects the transmission element against external influence.

The second housing part may be fixedly connected to the antenna unit. In particular, the first housing part may include multiple parts and the antenna unit may include at least one cover layer that is clamped between the aforementioned multiple parts of the first housing part.

A further embodiment of the MR local coil provides that the housing has a tongue and groove connection, wherein the second housing part is guided relative to the first housing part by the tongue and groove connection in a rotatable manner about the axis of rotation.

The tongue and groove connection may be circular, wherein the axis of rotation extends through the central point of the circle. For example, the first housing part has a projection that engages into a depression (e.g., groove), which extends around in a circle, of the second housing part. As a consequence, the second housing part may be guided in a stable manner relative to the first housing part during a rotation about the axis of rotation.

A further embodiment of the MR local coil provides that the housing has a stop that limits a possible rotational range about the axis of rotation. Advantageously, it is consequently possible to avoid an overloading of the transmission element on account of a rotation that is too intense.

A further embodiment of the MR local coil provides that the second housing part includes two parts that are connected to one another by screws and/or detents. This advantageously renders it possible to produce and/or to assemble the second housing part in a simple manner.

A further embodiment of the MR local coil provides that the MR local coil includes a rigid-flexible circuit board, wherein the transmission element is a flexible part of the rigid-flexible circuit board. The rigid-flexible circuit board includes a first rigid part connected by a first connection to the first housing part. The rigid-flexible circuit board further includes a second rigid part connected by a second connection to the second housing part.

Advantageously, the rigid-flexible circuit board is configured in such a manner that a signal transmission is also provided in the case of many rotation cycles. In particular, the rigid-flexible circuit board is configured in a space-saving manner as a possible cable-strand solution. Advantageously, in addition to guiding signals and/or energy, it is possible to integrate further functions (e.g., position sensor, amplifier, splitter, etc.) onto the rigid-flexible circuit board.

In particular, the flexible part has the shape of a ribbon that is arranged in a spiral manner about the axis of rotation. The first rigid part of the rigid-flexible circuit board is arranged on a first end of the ribbon and the second rigid part of the rigid-flexible circuit board is arranged on another end (the second end) of the ribbon.

The first connection and/or the second connection may be fixedly connected. In other words, the first and/or the second rigid parts of the rigid-flexible circuit board may be fixedly connected to the first or second housing part, respectively.

A further embodiment of the MR local coil provides that the first connection and/or the second connection are configured in a detachable manner, e.g., by an intermediate plug connection. Advantageously, this renders it possible to repair the MR local coil more easily. For example, using an intermediate plug connection to the second housing part, it is possible for the connection cable to be more easily exchanged. Advantageously, it is easy to fit the rigid-flexible circuit board with an intermediate plug connection and a rapid and secure exchange of the connection line, (e.g., during assembly or repair), is rendered possible.

A further embodiment of the MR local coil provides that the transmission element has a first end and a second end, wherein the transmission element is angled at the first end and/or at the second end, in particular by 90°. In particular, the flexible part of the rigid-flexible circuit board has a first end and a second end, wherein the transmission element is angled on the first end and on the second end, in particular by 90°.

Advantageously, as a consequence the transmission element may be guided out of a layer and/or plane of the spiral-shaped arrangement. This renders possible for example an easier connection to the connection cable and/or the antenna unit.

A further embodiment of the MR local coil provides that the first housing part and/or the second housing part includes a gap that extends perpendicular to the axis of rotation, wherein the transmission element is guided through the gap.

In particular, the angled first and/or second end of the transmission element may be guided through the slot. Advantageously, the gap is used as a carrier of the part of the transmission element, which is arranged in a spiral manner about the axis of rotation. In particular, the spiral tenses or relaxes as a consequence when the connection cable rotates relative to the antenna unit.

A further embodiment of the MR local coil provides that the housing includes a guiding element, wherein at least the part of the transmission element, which is arranged in a spiral manner about the axis of rotation, is arranged in the guiding element and is guided by the guiding element.

Moreover, a magnetic resonance apparatus having at least one MR local coil that is described above is proposed.

BRIEF DESCRIPTION OF THE DRAWINGS

Further advantages, features, and details of the disclosure are provided in the exemplary embodiments that are described below and also with reference to the drawings. Parts that correspond to one another are provided with the same reference characters in all the figures.

DETAILED DESCRIPTION

Figure 1:
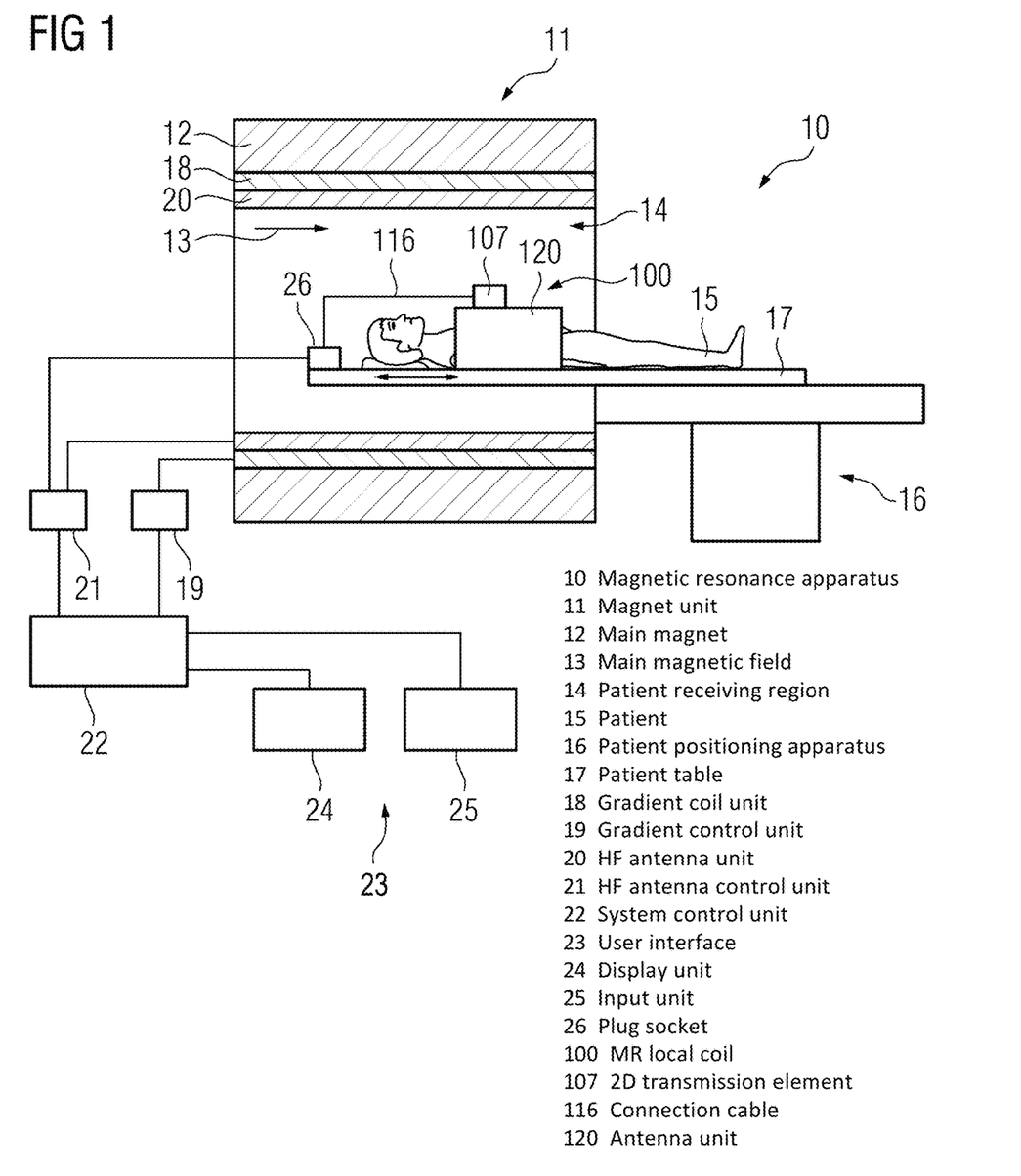
FIG. 1 depicts an example of a magnetic resonance (MR) apparatus having an MR local coil in a schematic representation.

A magnetic resonance apparatus 10 is illustrated schematically having an MR local coil 100 that is arranged on a patient 15. The magnetic resonance apparatus 10 includes a magnet unit 11 that has a main magnet 12 for generating an intense and in particular temporally constant main magnetic field 13. Moreover, the magnetic resonance apparatus 10 includes a patient receiving region 14 for receiving the patient 15. The patient receiving region 14 in the present exemplary embodiment is designed in a cylindrical manner and is surrounded in a peripheral direction in a cylindrical manner by the magnet unit 11. Fundamentally, however, a design of the patient receiving region 14 that differs from this is possible. The patient 15 may be pushed into the patient receiving region 14 by a patient positioning apparatus 16 of the magnetic resonance apparatus 10. The patient positioning apparatus 16 in this regard has a patient table 17 that is configured as movable within the patient receiving region 14.

The magnet unit 11 furthermore has a gradient coil unit 18 for generating magnetic field gradients that are used for a location encoding during imaging. The gradient coil unit 18 is controlled by a gradient control unit 19 of the magnetic resonance apparatus 10. The magnet unit 11 furthermore includes a high frequency antenna unit 20 that in the present exemplary embodiment is configured as a body coil that is fixedly integrated into the magnetic resonance apparatus 10. The high frequency antenna unit 20 is controlled by a high frequency antenna control unit 21 of the magnetic resonance apparatus 10 and radiates magnetic resonance sequences in the form of high frequency (HF) signals into an examination space that is formed from a patient receiving region 14 of the magnetic resonance apparatus 10. As a consequence, an excitation of atomic nuclei is set by the main magnetic field 13 that is generated by the main magnet 12. Magnetic resonance signals that are in turn HF signals are generated by relaxation of the excited atomic nuclei. The high frequency antenna unit 20 is configured to receive magnetic resonance signals. Moreover, the MR local coil includes an antenna unit 120 having antennas that are likewise configured to receive and/or to transmit HF signals. Advantageously, the antenna unit 120 is designed as flexible, for example, as a cover so that the antennas may be attached particularly close to the body of the patient 15.

In order to control the main magnet 12, the gradient control unit 19 and in order to control the high frequency antenna control unit 21, the magnetic resonance apparatus 10 has a system control unit 22. The system control unit 22 controls the magnetic resonance apparatus 10 in a centralized manner such as, for example, the implementation of a predetermined imaging gradient echo sequence. Moreover, the system control unit 22 includes an evaluating unit that is not further illustrated for evaluating the magnetic resonance signals that are detected during the magnetic resonance examination. Furthermore, the magnetic resonance apparatus 10 includes a user interface 23 connected to the system control unit 22. Control information such as, for example, imaging parameters, and also reconstructed magnetic resonance images may be displayed on a display unit 24, (e.g., on at least one monitor), of the user interface 23 for medical operating personnel. Furthermore, the user interface 23 has an input unit 25 by which information and/or parameters may be input during a measuring procedure by the medical operating personnel.

The MR local coil 100 is connected via a connection cable 116 to a plug socket of the magnetic resonance apparatus 10, the plug socket being arranged on the patient table 17, and signals and/or energy may be transmitted from and/or to the high frequency antenna control unit 21 via the plug socket.

A two-dimensional transmission element 107 is located at the connection site between the connection cable 116 and the antenna unit 120 of the MR local coil so as to transmit energy and/or signals between the connection cable 116 and the antenna unit 120 illustrated in detail in the following figures. In particular, in this case, an exemplary embodiment is illustrated as to how a mechanical and electrical connection from the connection cable to the antenna unit 120 of the MR local coil 100 may be configured in a rotatable manner.

Figure 2:
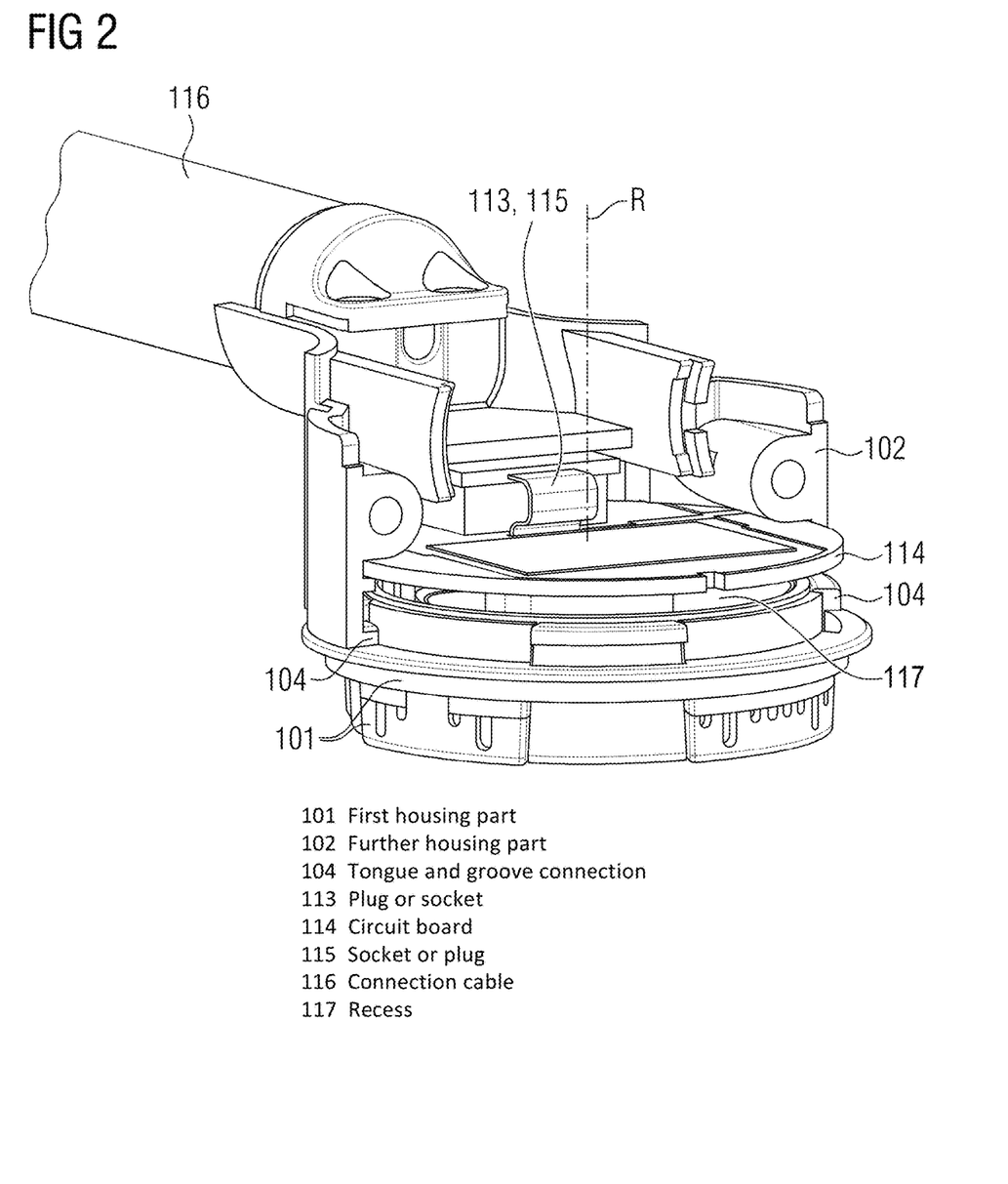
FIG. 2-3 depict an example of an arrangement having a transmission element for transmitting energy and/or signals between a connection cable and an antenna unit of the MR local coil.
Figure 3:
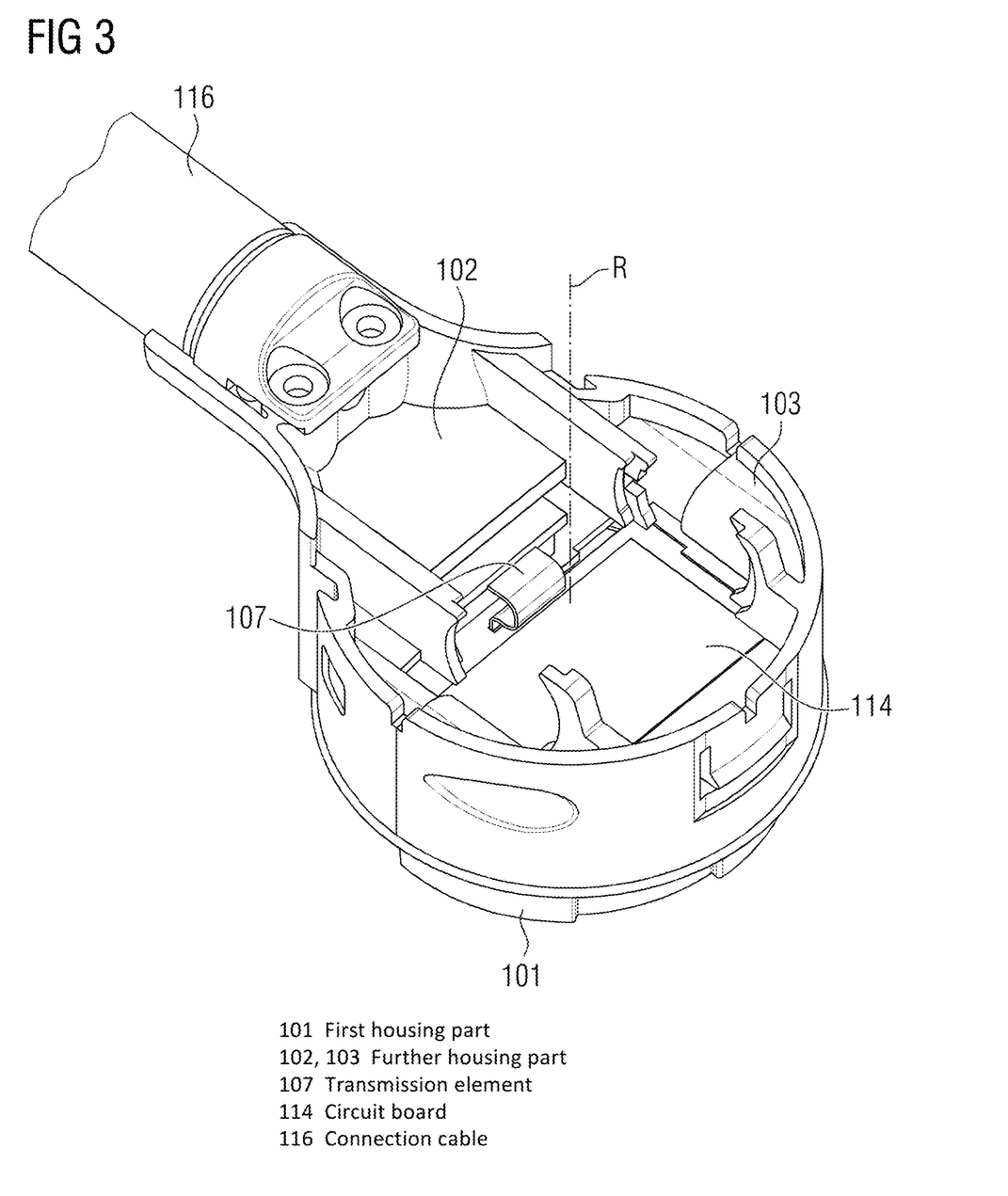

As is illustrated in FIGS. 2 and 3, the arrangement is of multiple housing parts that may rotate with respect to one another. A first housing part 101 is fixedly connected to the local coil. For this purpose, the first housing parts may include two parts and a cover layer of the antenna unit 120 may be clamped between the two parts.

A further housing part including two parts 102, 103 is rotatably mounted with respect to the first housing part 101. The rotating joint is realized via a tongue and groove connection 104. The first housing is divided into two parts 102 and 103 for improved mountability and is connected to one another for example via screws or detents. A stop between the rotating parts. In other words, the first housing part 101 and the second housing part 102, 103, may limit the angle of rotation.

Figure 4:
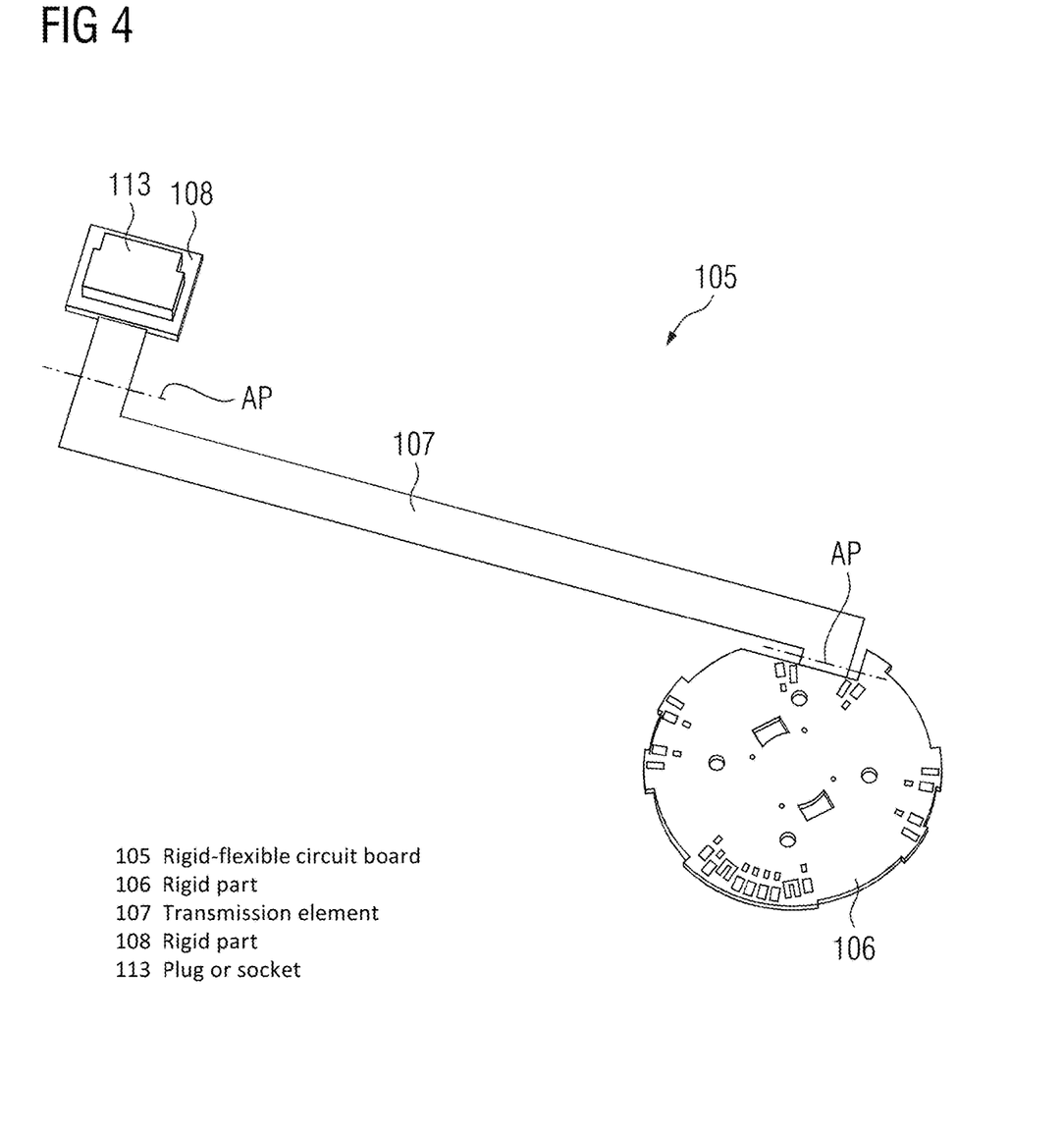
FIG. 4 depicts an example of a transmission element in a rolled-out state.

The contacting arrangement is provided via a rigid-flexible circuit board 105 that is illustrated in FIG. 4. The rigid-flexible circuit board 105 includes two rigid parts 106, 108 and also a flexible part in the form of a flexible circuit board that forms a two-dimensional transmission element 107.

The rigid part 106 is fixedly connected to the first housing part 101. The transmission element 107 forms a spiral owing to angling twice at the sites AP and rolling and the spiral may tense like a spiral spring by rotating, cf. FIG. 6, or may relax, cf. FIG. 5. The transmission element 107 is, in other words, in part arranged about an axis of rotation R in a spiral manner.

Figure 5:
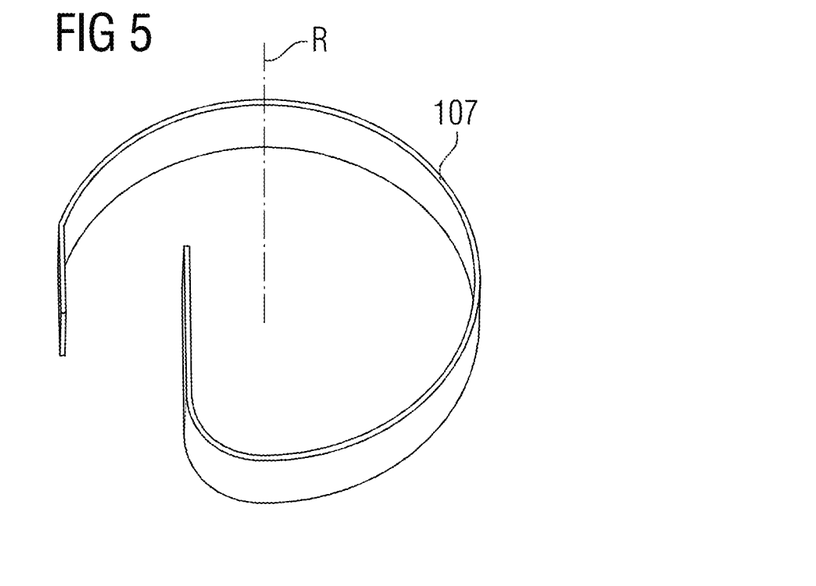
FIG. 5 depicts an example of a transmission element in spiral shape in a first rotation state.
Figure 6:
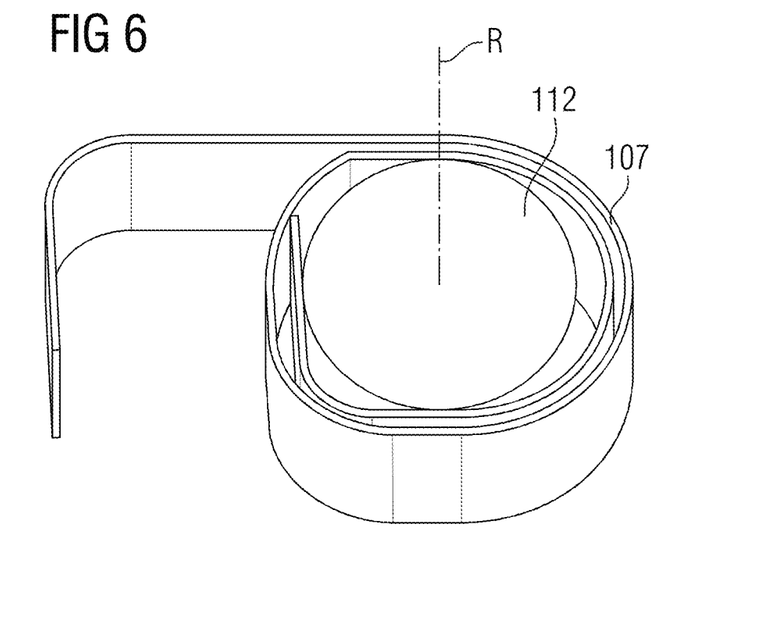
FIG. 6 depicts an example of a transmission element in spiral shape in a second rotation state.

The length of the transmission element 107 and the minimal winding diameter in the form of a limiting element 112, that prevents the conductor tracks of the transmission element 107 breaking on account of continuous tensing and relaxing of the spiral, defines the angle of rotation that may be achieved. The longer the flexible part the greater the angle of rotation that may be achieved by the connection cable 116 with respect to the antenna unit 120 of the MR local coil.

A circuit board 114 is arranged on the second housing part 102, 103 and the circuit board may rotate together with the second housing part 102, 103 with respect to the first housing part 101. The rigid part 108 of the rigid-flexible circuit board 105 includes a plug 113 (or a socket) that is plugged on the circuit board 114 in a socket 115 (or a plug) and consequently forms a detachable connection. This intermediate plug connection renders it possible to exchange the connection cable 116 of the MR local coil 100. It is also conceivable to omit this intermediate plug connection; then the rigid part 108 functionally corresponds to the rotatable circuit board 114. The connection cable 116, which connects the MR local coil 100 to the magnetic resonance apparatus 10, (e.g., by a solder connection), is connected to this rotatable circuit board 114. The rotatable circuit board 114 allows a more delicate assembly and is easy to install via the intermediate plug connection during final assembly of the MR local coil 100.

Figure 7:
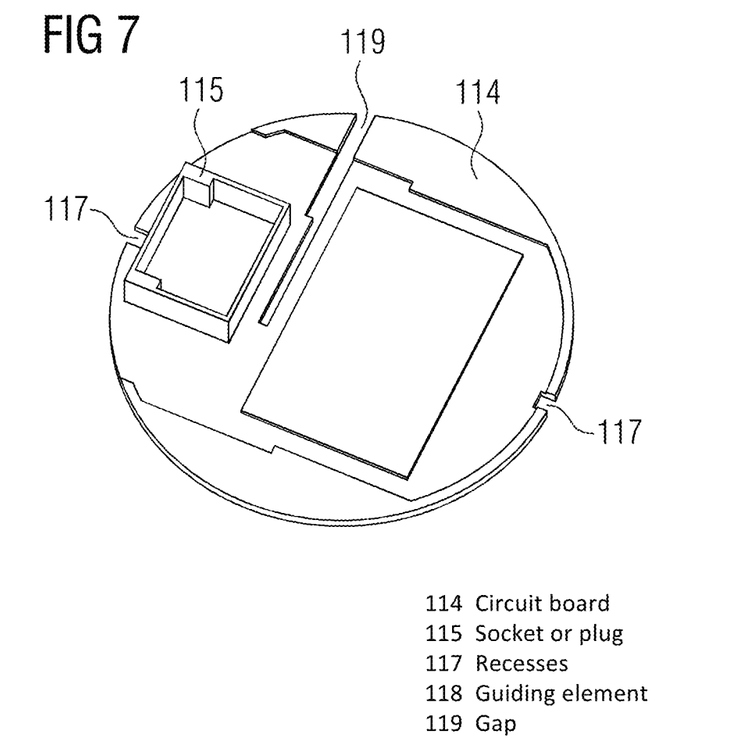
FIG. 7 depicts an example of an element of the arrangement having a gap in which the transmission element is guided.
Figure 8:
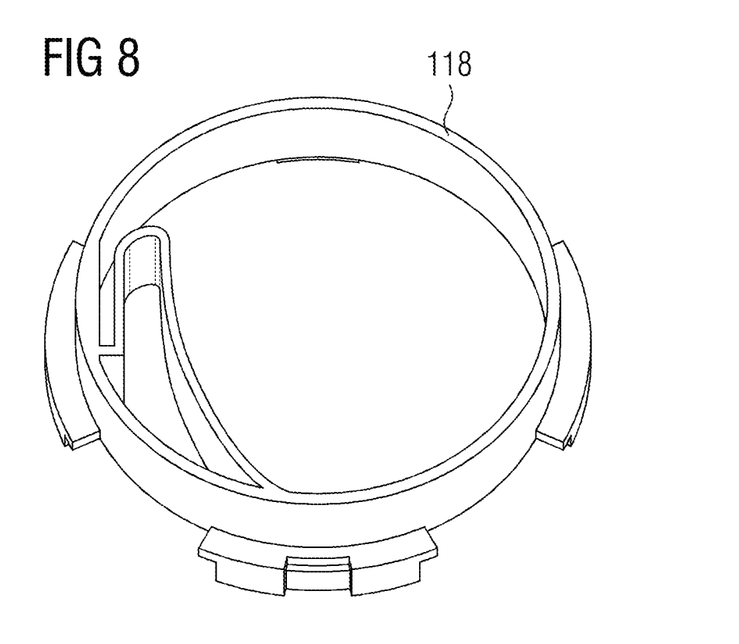
FIG. 8 depicts an example of an intermediate housing for receiving the transmission element.

As is apparent in FIG. 7, the rotatable circuit board 114 has recesses 117 that form a positive-locking connection with spigots in the parts 102 and 103 of the second housing part. This positive-locking connection functions as a carrier between the circuit board 114 and the second housing part 102, 103. The circuit board 114 has a gap 119. The angled end of the transmission element 107 is pushed into this gap 119 with the rigid part 108 and thus arrives at the plug 113 of the intermediate plug connection. This gap 119 is used as a carrier of the spiral-shaped transmission element 107 that consequently tenses and relaxes when the circuit board 114 is rotated, cf. FIGS. 5 and 6. An intermediate housing, as is illustrated in FIG. 8, is used as a guiding element 118 in which the spiral-shaped transmission element 107 may tense and relax. Moreover, the intermediate housing is used so as to guide the transmission element. The intermediate housing is fixedly connected to the first housing part 101.

The ability to rotate may bring the output of the connection cable 116 from the MR local coil 100 into the optimal position with respect to the plug socket 26 of the magnetic resonance apparatus. This improves the handling and optimizes the location of the connection cable 116 on the patient 15. It is possible, owing to the connection cable 116 configured in a rotatable manner, for the necessary cable length to be shortened. It follows from this in particular that fewer decoupling coils are required for the connection cable 116. As a consequence, the flexibility of the connection cable 116 increases (the region of the decoupling coil stiffens the connection cable 116) and the weight of the connection cable decreases.

In conclusion, reference is once again made to the fact that the MR local coil that is described in detail above and the magnetic resonance apparatus are merely exemplary embodiments that may be modified by the person skilled in the art in various ways without departing from the scope of the disclosure. Furthermore, the use of the indefinite article "a" or "an" does not rule out that the relevant features may also be provided multiple times. Likewise, the term "unit" does not rule out that the relevant components are provided from multiple cooperating part components that may also likewise be spatially distributed where applicable.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the disclosure has been illustrated and described in detail with the help of the embodiments, the disclosure is not limited to the disclosed examples. Other variations may be deduced by those skilled in the art without leaving the scope of protection of the claimed disclosure.

The invention claimed is:

1. A magnetic resonance (MR) local coil comprising:
   an antenna unit having at least one antenna configured to receive and/or transmit high frequency (HF) signals;
   a connection cable configured to connect the MR local coil to a magnetic resonance apparatus; and
   a two-dimensional transmission element configured to transmit energy and/or signals between the connection cable and the antenna unit,
   wherein the two-dimensional transmission element is at least in part arranged about an axis of rotation in a spiral-shaped arrangement.

2. A magnetic resonance (MR) local coil comprising:
   an antenna unit having at least one antenna configured to receive and/or transmit high frequency (HF) signals;
   a connection cable configured to connect the MR local coil to a magnetic resonance apparatus;
   a rigid-flexible circuit board;
   a housing having a first housing part and a second housing part; and a two-dimensional transmission element arranged in the housing and configured to transmit energy and/or signals between the connection cable and the antenna unit,
wherein the two-dimensional transmission element is at least in part arranged about an axis of rotation in a spiral-shaped arrangement,
wherein the two-dimensional transmission element is a flexible part of the rigid- flexible circuit board,
wherein the rigid-flexible circuit board comprises a first rigid part connected by a first connection to the first housing part,
wherein the rigid-flexible circuit board comprises a second rigid part connected by a second connection to the second housing part, and
wherein the second housing part is configured to be rotated relative to the first housing part about the axis of rotation.

3. A magnetic resonance (MR) apparatus comprising:
at least one MR local coil having:
an antenna unit having at least one antenna configured to receive and/or transmit high frequency (HF) signals;
a connection cable configured to connect the MR local coil to a magnetic resonance apparatus; and
a two-dimensional transmission element configured to transmit energy and/or signals between the connection cable and the antenna unit,
wherein the two-dimensional transmission element is at least in part arranged about an axis of rotation in a spiral-shaped arrangement.

4. The MR local coil of claim 1, wherein the two-dimensional transmission element comprises a flexible circuit board and/or a two-dimensional ribbon cable.

5. The MR local coil of claim 1, wherein the antenna unit comprises multiple antennas, and
wherein the two-dimensional transmission element comprises multiple electrical and/or optical conductors arranged adjacent to one another in order to transmit signals of the multiple antennas.

6. The MR local coil of claim 1, wherein the antenna unit is two-dimensional.

7. The MR local coil of claim 1, wherein the antenna unit is flexible.

8. The MR local coil of claim 1, further comprising:
a housing having a first housing part and a second housing part,
wherein the two-dimensional transmission element is arranged in the housing, and
wherein the second housing part is configured to be rotated relative to the first housing part about the axis of rotation.

9. The MR local coil of claim 2, wherein the first connection and/or the second connection is/are configured in a detachable manner.

10. The MR local coil of claim 1, wherein the spiral-shaped arrangement of the two-dimensional transmission element has a first end and a second end around the axis of rotation, and
wherein the two-dimensional transmission element is angled at the first end and/or at the second end.

11. The MR local coil of claim 1, wherein the spiral-shaped arrangement comprises a curve or spiral line that extends about the axis of rotation.

12. The MR local coil of claim 8, wherein the housing comprises a tongue and groove connection, and
wherein the second housing part is configured to be guided relative to the first housing part by the tongue and groove connection in a rotatable manner about the axis of rotation.

13. The MR local coil of claim 8, wherein the housing comprises a stop and/or a limiting element arranged within the spiral-shaped arrangement of the two-dimensional transmission element, and
wherein the stop is configured to limit a rotational range about the axis of rotation.

14. The MR local coil of claim 8, wherein the first housing part and/or the second housing part comprises a gap that extends perpendicular to the axis of rotation, and
wherein the two-dimensional transmission element is guided through the gap.

15. The MR local coil of claim 8, wherein the housing comprises a guiding element, and
wherein at least a part of the two-dimensional transmission element is arranged in a spiral manner about the axis of rotation is arranged in the guiding element and is guided by the guiding element.

16. The MR local coil of claim 10, wherein the two-dimensional transmission element is angled at the first end and/or the second end by 90°.

17. The MR local coil of claim 12, wherein the housing further comprises a stop and/or a limiting element arranged within the spiral-shaped arrangement of the two-dimensional transmission element, and
wherein the stop is configured to limit a rotational range about the axis of rotation.

18. The MR local coil of claim 17, further comprising:
a rigid-flexible circuit board,
wherein the two-dimensional transmission element is a flexible part of the rigid-flexible circuit board,
wherein the rigid-flexible circuit board comprises a first rigid part connected by a first connection to the first housing part, and
wherein the rigid-flexible circuit board comprises a second rigid part connected by a second connection to the second housing part.

19. The MR local coil of claim 18, wherein the first connection and/or the second connection is/are configured in a detachable manner.

* * * * *